US010231929B2

(12) United States Patent
Nomura et al.

(10) Patent No.: US 10,231,929 B2
(45) Date of Patent: Mar. 19, 2019

(54) SOLID DISPERSION

(71) Applicant: TAKEDA PHARMACEUTICAL COMPANY LIMITED, Osaka (JP)

(72) Inventors: Yukihiro Nomura, Osaka (JP); Yuki Tsushima, Osaka (JP); Yutaka Ebisawa, Osaka (JP)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 0 days.

(21) Appl. No.: 15/126,334

(22) PCT Filed: Mar. 17, 2015

(86) PCT No.: PCT/JP2015/057855
§ 371 (c)(1),
(2) Date: Sep. 15, 2016

(87) PCT Pub. No.: WO2015/141662
PCT Pub. Date: Sep. 24, 2015

(65) Prior Publication Data
US 2017/0079915 A1  Mar. 23, 2017

(30) Foreign Application Priority Data
Mar. 18, 2014  (JP) .................... 2014-055543

(51) Int. Cl.
| *A61K 9/14* | (2006.01) |
| *B29B 9/10* | (2006.01) |
| *B01J 2/22* | (2006.01) |
| *A61K 31/501* | (2006.01) |
| *A61K 31/4422* | (2006.01) |
| *B29K 1/00* | (2006.01) |
| *B29K 105/00* | (2006.01) |

(52) U.S. Cl.
CPC .............. *A61K 9/146* (2013.01); *A61K 9/145* (2013.01); *A61K 31/4422* (2013.01); *A61K 31/501* (2013.01); *B01J 2/22* (2013.01); *B29B 9/10* (2013.01); *B29K 2001/08* (2013.01); *B29K 2105/0035* (2013.01)

(58) Field of Classification Search
CPC .... A61K 9/146; A61K 9/145; A61K 31/4422; A61K 31/501; B01J 2/22; B29B 9/10; B29K 2001/08; B29K 2105/0035
USPC .................................................. 514/252.05
See application file for complete search history.

(56) References Cited

U.S. PATENT DOCUMENTS

| 5,456,923 A | 10/1995 | Nakamichi et al. |
| 2004/0058956 A1 | 3/2004 | Akiyama et al. |
| 2009/0053315 A1 | 2/2009 | Brough et al. |
| 2010/0197651 A1 | 8/2010 | Taniguchi et al. |
| 2011/0306632 A1 | 12/2011 | Miller et al. |
| 2013/0142877 A1 | 6/2013 | Nalawade et al. |

FOREIGN PATENT DOCUMENTS

| EP | 1 967 181 | 9/2008 |
| JP | 7-324086 | 12/1995 |
| JP | 2000-309588 | 11/2000 |
| JP | 2004-67606 | 3/2004 |
| JP | 2004-534822 | 11/2004 |
| JP | 2010-502645 | 1/2010 |
| WO | 02/47723 | 6/2002 |
| WO | 02/48141 | 6/2002 |
| WO | 02/100379 | 12/2002 |
| WO | 03/000292 | 1/2003 |
| WO | 2006/006691 | 1/2006 |
| WO | 2007/027494 | 3/2007 |
| WO | 2008/027993 | 3/2008 |
| WO | 2008/120724 | 10/2008 |
| WO | 2015/103230 | 7/2015 |

OTHER PUBLICATIONS

English translation of JP 2004-67606 A, translated on Mar. 8, 2018 (Year: 2018).*
International Preliminary Report on Patentability dated Sep. 20, 2016 in corresponding International (PCT) Application No. PCT/JP2015/057855, with English translation.
International Search Report dated May 19, 2015 in International Application No. PCT/JP2015/057855.
Nikghalb, L.A. et al., "Solid Dispersion: Methods and Polymers to increase the solubility of poorly soluble drugs", Journal of Applied Pharmaceutical Science, 2012, vol. 2, No. 10, p. 170-175.
Tran, T. TD. et al., "The roles of acidifiers in solid dispersions and physical mixtures", International Journal of Pharmaceutics, 2010, vol. 384, p. 60-66.
Mogal, S.A. et al., "Solid dispersion technique for improving solubility of some poorly soluble drugs", Der Pharmacia Lettre, 2012, vol. 4, No. 5, p. 1574-1586.
Office Action dated Aug. 10, 2018 in Chinese Patent Application No. 201580020406.9.
Industrial Pharmaceutics, the second edition, Weisan Pan. Beijing, The Medicine Science and Technology Press of China, pp. 368-369 (Jun. 30, 2010).
Handbook of Fine chemical industry product: Drugs, Xueliang Zhou, Beijing, the Chemical Industry Press, p. 173 (Jan. 31, 2003).
Extended European Search Report dated Sep. 18, 2017 in European Application No. 15764152.3.

* cited by examiner

*Primary Examiner* — Kristin A Vajda
(74) *Attorney, Agent, or Firm* — Wenderoth, Lind & Ponack, L.L.P.

(57) ABSTRACT

A solid dispersion for achieving improved solubility and absorbability of a pharmaceutically active ingredient, which contains (1) an amorphous pharmaceutically active ingredient, (2) one or more substances selected from among methyl cellulose and organic acids and (3) an enteric base material. In cases where methyl cellulose is contained therein, the solid dispersion does not contain any water-soluble polymer other than methyl cellulose.

12 Claims, 5 Drawing Sheets

[FIG. 1]
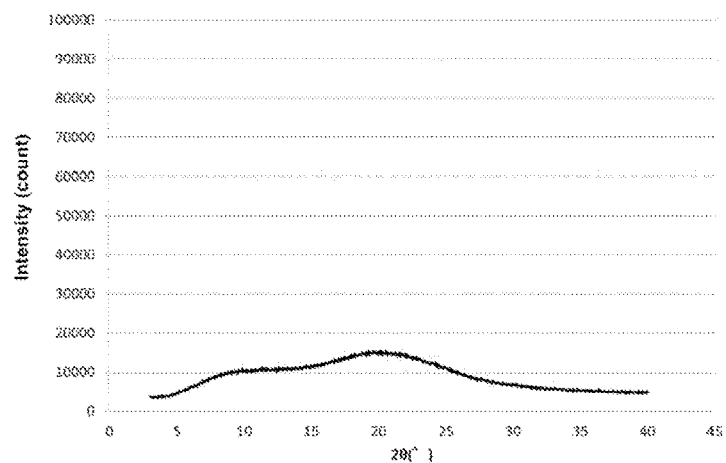
[FIG. 2]
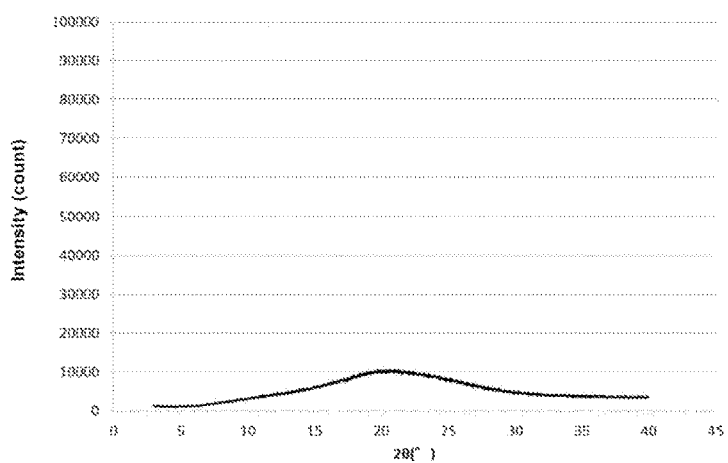
[FIG. 3]
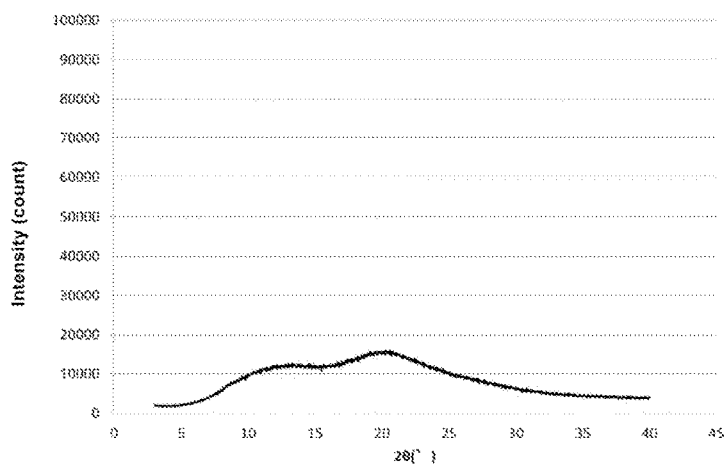

[FIG. 4]
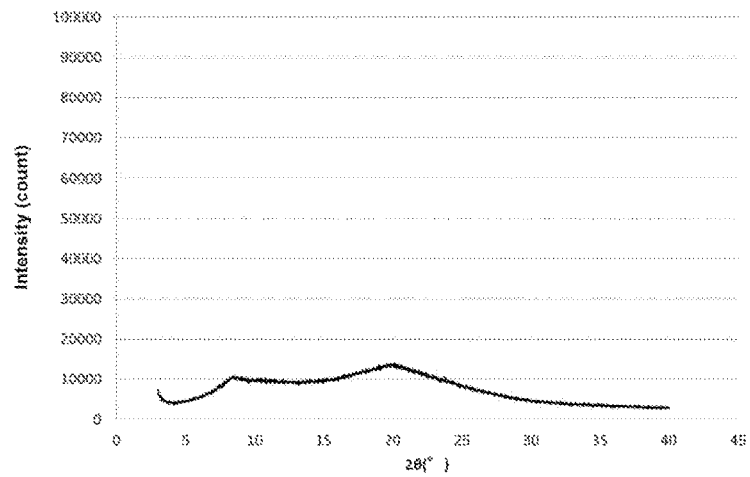
[FIG. 5]
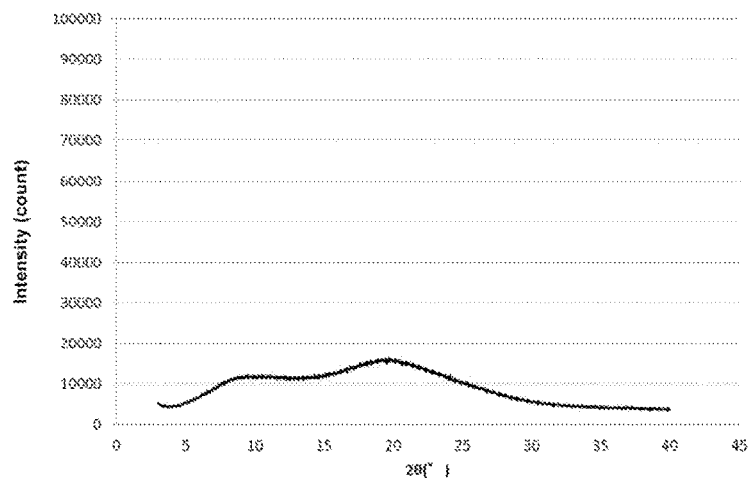
[FIG. 6]
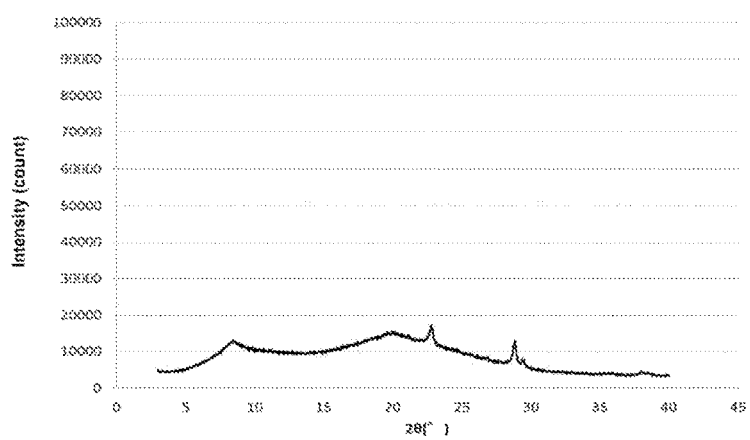

[FIG. 7]
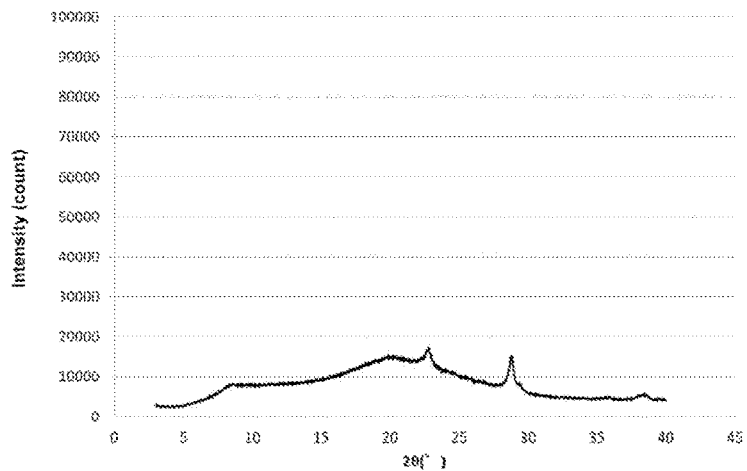
[FIG. 8]
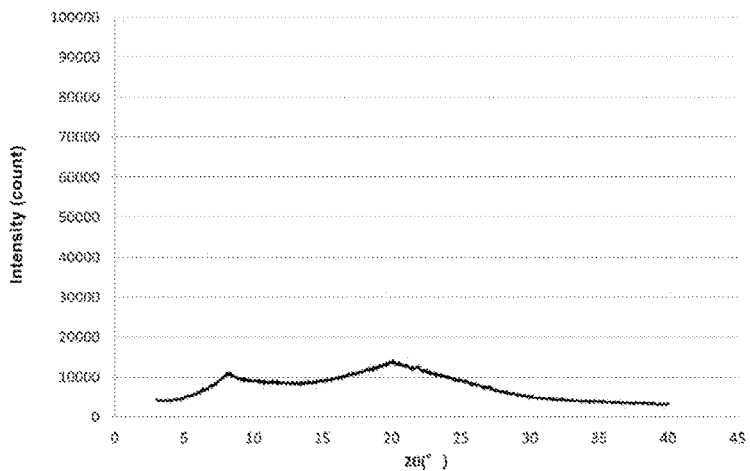
[FIG. 9]
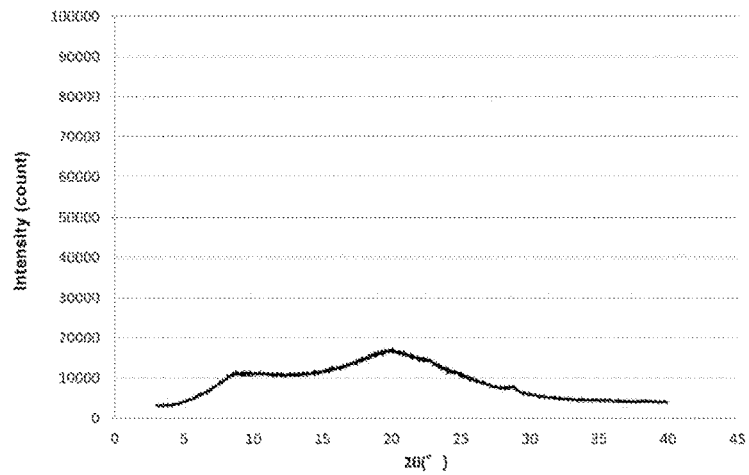

[FIG. 10]
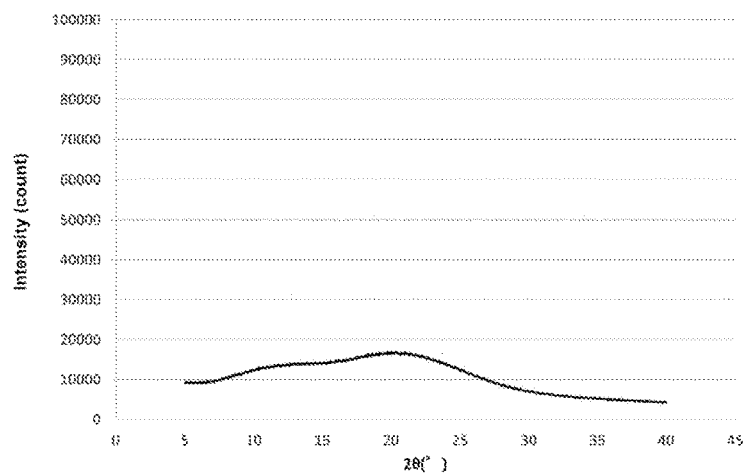
[FIG. 11]
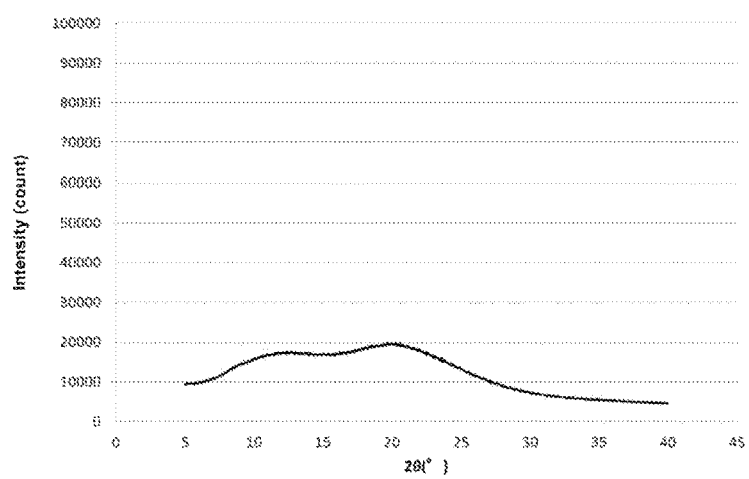
[FIG. 12]
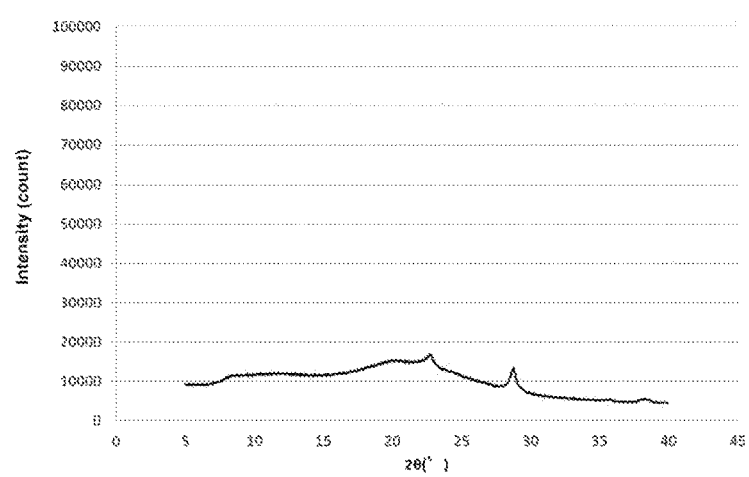

[FIG. 13]
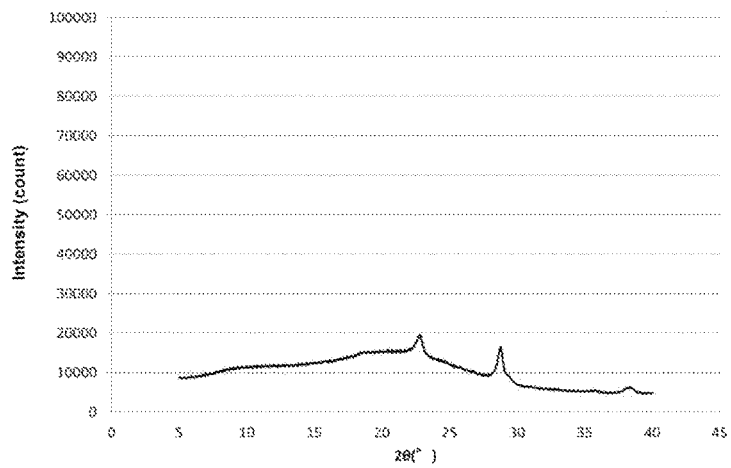
[FIG. 14]
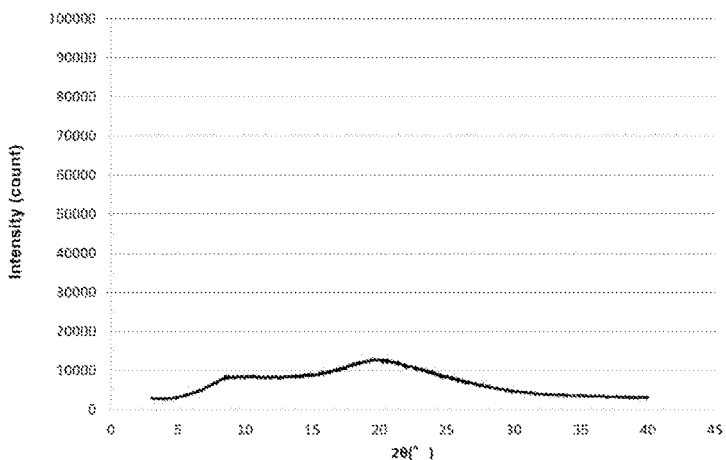
[FIG. 15]
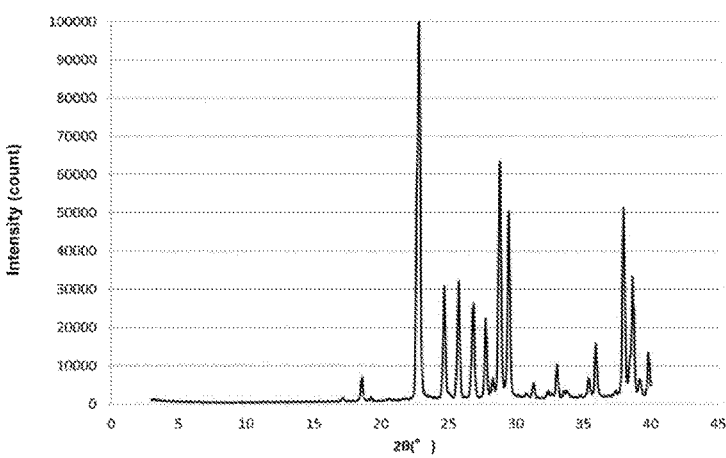

SOLID DISPERSION

TECHNICAL FIELD

The present invention relates to a solid dispersion. Specifically, the present invention relates to a solid dispersion having enhanced solubility and absorption properties of an active pharmaceutical ingredient. The present invention also relates to a method of producing the solid dispersion, a pharmaceutical composition containing the solid dispersion, and pharmaceutical use of the solid dispersion.

BACKGROUND ART

Use of a solid dispersion in a pharmaceutical is a technique effective for improving the solubility and absorption properties of an active pharmaceutical ingredient (hereinafter sometimes referred to as "API"), and for enhancing bioavailability of the active pharmaceutical ingredient.

Reports have been already made on solid dispersions, and Patent Literature 1, for example, discloses a solid dispersion that is a pharmaceutical composition containing a poorly water-soluble or water-insoluble HER2 inhibitory substance, and having improved water solubility of the HER2 inhibitory substance.

Patent Literature 2 discloses a pharmaceutical composition containing a poorly water-soluble or water-insoluble lipid rich plaque retracting substance, and having improved water solubility of the lipid rich plaque retracting substance, and Patent Literature 3 discloses a method of producing a solid dispersion wherein a solid substance and a solvent in an amount sufficient to reduce the melting point of the solid substance are hot-melted. Moreover, Patent Literature 4 discloses a solid dispersion containing a p 38 MAP kinase inhibitor.

Furthermore, Patent Literature 5 discloses a solid dispersion comprising a thiazolidine derivative having a specific chemical structure or a salt thereof, a water-soluble polymer (excluding, however, hydroxypropylmethylcellulose and methyl cellulose), and hydroxypropylmethylcellulose and/or methyl cellulose, wherein these ingredients are contained at specific weight ratios.

Patent Literature 6 discloses a solid dispersion preparation containing cilnidipine or a pharmacologically acceptable salt thereof, and at least one water-soluble polymer selected from the group consisting of methyl cellulose, hydroxypropylmethylcellulose, and the like.

Patent Literature 7 discloses a solid dispersion useful as an agent for treating a disease in which dopamine $D_4$ receptor is involved, the solid dispersion comprising a 2-carbonylthiazole derivative, at least one water-soluble polymer selected from hydroxypropylmethylcellulose, hydroxypropylcellulose, polyvinylpyrrolidone, and methylcellulose, and an acid that is an inorganic acid or an organic acid.

CITATION LIST

Patent Literature

Patent Literature 1: WO 02/48141
Patent Literature 2: WO 02/47723
Patent Literature 3: WO 02/100379
Patent Literature 4: WO 2006/006691
Patent Literature 5: JP 7-324086 A
Patent Literature 6: WO 2008/120724
Patent Literature 7: JP 2000-309588 A

SUMMARY OF INVENTION

Technical Problem

Although findings about solid dispersions have been reported as described above, the conventional solid dispersions do not provide sufficient solubilities and absorption properties of the active pharmaceutical ingredients. This can also be understood from the fact that it has been suggested that, for example, with regard to a solid dispersion in which a certain water-soluble polymer is used, because the release of the drug also begins in the stomach, the pharmaceutical ingredient is recrystallized and precipitated before reaching the site of absorption (European Journal of Pharmaceuticals and Biopharmaceutical, 50 (2000) 47-60).

It is thus desired to provide a solid dispersion having enhanced solubility and absorption properties of an active pharmaceutical ingredient.

Solution to Problem

The present inventors found that a composition having excellent dissolution properties can be produced by providing a solid dispersion by adding, to a poorly water-soluble or water-insoluble compound, an enteric base material and methyl cellulose, an enteric base material and an organic acid, or an enteric base material, methyl cellulose, and an organic acid. As a result of further continued research, the present inventors completed the present invention. That is, the present invention relates to at least the following inventions [1] to [15].

[1] A solid dispersion containing:
  (1) an amorphous active pharmaceutical ingredient;
  (2) one or more selected from methyl cellulose and organic acids; and
  (3) an enteric base material, wherein
  when the solid dispersion contains methyl cellulose, the solid dispersion does not contain a water-soluble polymer other than methyl cellulose.

[2] The solid dispersion according to [1] above, wherein a supersaturation state is maintained.

[3] The solid dispersion according to [1] or [2] above, wherein the active pharmaceutical ingredient has a melting point not lower than about 80° C. and not higher than about 350° C.

[4] The solid dispersion according to any of [1] to [3] above, wherein the active pharmaceutical ingredient has a water solubility of less than 10 mg/mL at about 37° C.

[5] The solid dispersion according to any of [1] to [4] above, which is produced by a hot-melt extrusion method (HME method).

[6] The solid dispersion according to any of [1] to [5] above, wherein the solid dispersion contains methyl cellulose, with a weight ratio of methyl cellulose to the active pharmaceutical ingredient being about 1% to 3000%.

[7] The solid dispersion according to any of [1] to [6] above, which contains one or more organic acids.

[8] The solid dispersion according to any of [1] to [7] above, wherein the enteric base material is one or more enteric base materials selected from hydroxypropylmethylcellulose phthalate, hydroxypropylmethylcellulose acetate succinate, and methacrylic acid copolymers.

[9] The solid dispersion according to [7] above, wherein the organic acid is selected from fumaric acid, citric acid, succinic acid, and tartaric acid.

[10] The solid dispersion according to any of [1] to [9] above, wherein the active pharmaceutical ingredient is a poorly water-soluble or water-insoluble central nervous system enzyme inhibitory substance or vasodilator.

[11] A pharmaceutical containing the solid dispersion according to any of [1] to [10] above.

[12] A method of maintaining, in a solid dispersion produced by a hot-melt extrusion method (HME method), the solid dispersion containing an amorphous active pharmaceutical ingredient, one or more selected from methyl cellulose and organic acids, and an enteric base material, wherein when the solid dispersion contains methyl cellulose, the solid dispersion does not contain a water-soluble polymer other than methyl cellulose, a supersaturation state of the active pharmaceutical ingredient.

[13] A method of producing a solid dispersion containing an amorphous active pharmaceutical ingredient, one or more selected from methyl cellulose and organic acids, and an enteric base material, wherein when the solid dispersion contains methyl cellulose, the solid dispersion does not contain a water-soluble polymer other than methyl cellulose.

[14] A method of producing a solid dispersion including the step of forming a kneaded product containing an amorphous active pharmaceutical ingredient, one or more selected from methyl cellulose and organic acids, and an enteric base material (when the kneaded product contains methyl cellulose, the kneaded product does not contain a water-soluble polymer other than methyl cellulose).

[15] A method of producing a solid dispersion including the step of forming a kneaded product containing an amorphous active pharmaceutical ingredient, one or more selected from methyl cellulose and organic acids, and an enteric base material, using a hot-melt extrusion method (when the kneaded product contains methyl cellulose, the kneaded product does not contain a water-soluble polymer other than methyl cellulose).

Advantageous Effects of Invention

According to the present invention, there is provided a solid dispersion having enhanced solubility and absorption properties of an active pharmaceutical ingredient. The solid dispersion of the present invention exhibits enhanced dissolution properties of the poorly water-soluble or water-insoluble API through its supersaturation, to thereby achieve the maintenance of a high area under the blood concentration-time curve (AUC) at a small dose. The solid dispersion of the present invention therefore attains particularly advantageous effects in terms of drug efficacy.

BRIEF DESCRIPTION OF DRAWINGS

FIG. 1 shows results of X-ray powder diffraction of Comparative Example 1.
FIG. 2 shows results of X-ray powder diffraction of Comparative Example 2.
FIG. 3 shows results of X-ray powder diffraction of Comparative Example 3.
FIG. 4 shows results of X-ray powder diffraction of Example 1.
FIG. 5 shows results of X-ray powder diffraction of Example 2.
FIG. 6 shows results of X-ray powder diffraction of Example 3.
FIG. 7 shows results of X-ray powder diffraction of Example 4.
FIG. 8 shows results of X-ray powder diffraction of Example 5.
FIG. 9 shows results of X-ray powder diffraction of Example 6.
FIG. 10 shows results of X-ray powder diffraction of Example 7.
FIG. 11 shows results of X-ray powder diffraction of Example 8.
FIG. 12 shows results of X-ray powder diffraction of Example 9.
FIG. 13 shows results of X-ray powder diffraction of Example 10.
FIG. 14 shows results of X-ray powder diffraction of Example 11.
FIG. 15 shows results of X-ray powder diffraction of fumaric acid.

DETAILED DESCRIPTION OF INVENTION

The present invention will be hereinafter described in more detail.

[Amorphous Active Pharmaceutical Ingredient]

The amorphous active pharmaceutical ingredient of the ingredients contained in the solid dispersion of the present invention, which is an active pharmaceutical ingredient in an amorphous state, may not be completely amorphous, and may be in a state that is not generally recognized as a crystalline state.

One or more active pharmaceutical ingredients may be used as the active pharmaceutical ingredient of the present invention. These active pharmaceutical ingredients are not particularly limited in terms of properties, and may be any water-soluble, poorly water-soluble, or water-insoluble solid substances. The "poorly water-soluble or water-insoluble" means that the solid substance has a water solubility at 37° C., for example, of 10 mg/mL or less, and preferably 0.1 mg/mL or less. The water solubility of the active pharmaceutical ingredient may or may not be pH-dependent. Solubility can be measured in accordance with a conventional method.

Examples of water-soluble active pharmaceutical ingredients include, but are not particularly limited to, the following:

(1) Antibiotics: tetracycline hydrochloride, ampicillin, piperacillin, and the like. (2) Antipyretics/analgesics/antiphlogistics: sodium salicylate, sulpyrine, indomethacin sodium, morphine hydrochloride, and the like. (3) Antitussives and expectorants: ephedrine hydrochloride, noscapine hydrochloride, codeine phosphate, dihydrocodeine phosphate, isoproterenol hydrochloride, and the like. (4) Sedatives: chlorpromazine hydrochloride, atropine sulfate, and the like. (5) Antiulcer agents: metoclopramide, histidine hydrochloride, and the like. (6) Antiarrhythmics: propranolol hydrochloride, alprenolol hydrochloride, and the like. (7) Antihypertensive diuretics: hexamethonium bromide, clonidine hydrochloride, and the like. (8) Anticoagulants: heparin sodium, sodium citrate, and the like.

Examples of poorly water-soluble or water-insoluble active pharmaceutical ingredients include, but are not particularly limited to, the following:

(1) Antipyretic, analgesic, and antiinflammatory agents: for example, salicylic acid, sulpyrine, flufenamic acid, diclofenac, indomethacin, atropine, scopolamine, morphine, pethidine, levorphanol, ketoprofen, naproxen, ibuprofen, oxymorphone, aspirin, aminopyrine, phenacetin, acetaminophen, phenylbutazone, ketophenylbutazone, mefenamic acid, bucolome, benzydamine, mepirizole, tialamide, tinoridine, xylocaine, pentazocine, dexamethasone, hydrocortisone, prednisolone, azulene, isopropylantipyrine, sasapyrine, clofezone, Etodolac, and salts thereof (2) Tranquilizers: for example, diazepam, lorazepam, oxazepam, oxazolam, clotiazepam, medazepam, temazepam, fludiazepam, meprobamate, nitrazepam, and chlordiazepoxide. (3) Antipsychotic agents: for example, chlorpromazine, prochlorperazine, trifluoperazine, sulpiride, clocapramine hydrochloride, zotepine, haloperidol, and 1-[2-fluoro-4-(1H-pyrazole-1-yl)phenyl]-5-methoxy-3-(1-phenyl-1H-pyrazole-5-yl)pyridazin-4(1H)-one. (4) Antibacterial agents: for example, griseofulvin, lankacidins [J. Antibiotics, 38,877-885 (1985)], azole-based compounds [2-[(1R,2R)-2-(2,4-difluorophenyl)-2-hydroxy-1-methyl-3-(1H-1,2,4-triazole-1-yl)propyl]-4-[4-(2,2,3,3-tetrafluoropropoxy)phenyl-3-(2H, 4H)-1,2,4-triazoline, fluconazole, itraconazole, and the like], nalidixic acid, piromidic acid, pipemidic acid trihydrate, enoxacin, cinoxacin, ofloxacin, norfloxacin, ciprofloxacin hydrochloride, and sulfamethoxazole-trimethoprim. (5) Antibiotics: for example, gentamicin, dibekacin, kanendomycin, lividomycin, tobramycin, amikacin, dibekacin, fradiomycin, sisomicin, tetracycline, oxytetracycline, rolitetracycline, doxycycline, ampicillin, piperacillin, ticarcillin, cephalothin, cefaloridine, cefotiam, cefotiam hexetil, cefsulodin, cefmenoxime, cefmetazole, cefazolin, cefotaxime, cefoperazone, ceftizoxime, moxalactam, thienamycin, sulfazecin, aztreonam, amoxicillin, cefalexin, erythromycin, bacampicillin, minocycline, chloramphenicol, and salts thereof (6) Antitumor agents: for example, 6-O—(N-chloroacetylcarbamoyl)fumagillol, bleomycin, methotrexate, actinomycin-D, mitomycin-C, daunorubicin, adriamycin, neocarzinostatin, cytosine arabinoside, fluorouracil, tetrahydrofuryl-5-fluorouracil, Picibanil, lentinan, levamisole, bestatin, azimexon, glycyrrhizin, HER2 inhibitor (e.g., heterocyclic compounds described in WO 01/77107 and the like), taxol, doxorubicin hydrochloride, etoposide, mitoxantrone, mesna, dimesna, aminoglutethimide, tamoxifen, acrolein, cisplatin, carboplatin, cyclophosphamide, lomustine (CCNU), and carmustine (BCNU). (7) Antihyperlipidemic agents: for example, clofibrate, 2-chloro-3-[4-(2-methyl-2-phenylpropoxy)phenyl]ethyl propionate [Chem. Pharm. Bull, 38-2792-2796 (1990)], clinofibrate, colestyramine, soysterol, tocopherol nicotinate, nicomol, niceritrol, probucol, and elastase.

(8) Antitussives and expectorants: for example, ephedrine, methylephedrine, noscapine, codeine, dihydrocodeine, alloclamide, chlorfedianol, picoperidamine, cloperastine, protokylol, isoproterenol, salbutamol, terbutaline, bromhexine, carbocysteine, ethylcysteine, methylcysteine, and salts thereof (9) Muscle relaxants: for example, pridinol, tubocurarine, pancuronium, chlorphenesin carbamate, tolperisone hydrochloride, eperisone hydrochloride, tizanidine hydrochloride, mephenesin, chlorzoxazone, phenprobamate, methocarbamol, chlormezanone, pridinol mesilate, afloqualone, baclofen, and dantrolene sodium. (10) Antiepileptic agents: for example, phenytoin, ethosuximide, acetazolamide, chlordiazepoxide, phenobarbital, carbamazepine, and primidone. (11) Antiulcer agents: for example, lansoprazole, metoclopramide, famotidine, omeprazole, sulpiride, trepibutone, cetraxate hydrochloride, gefarnate, irsogladine maleate, cimetidine, ranitidine hydrochloride, nizatidine, and roxatidine acetate hydrochloride. (12) Antidepressants: for example, imipramine, clomipramine, noxiptiline, and phenelzine. (13) Antiallergic agents: for example, diphenhydramine, chlorpheniramine, tripelenamine, methodiramine, clemizole, diphenylpyraline, methoxyphenamine, clemastine fumarate, cyproheptadine hydrochloride, mequitazine, and alimemazine tartrate. (14) Cardiotonic agents: for example, trans-pi-oxocamphor, theophyllol, aminophylline, and etilefrine. (15) Antiarrhythmic agents: for example, propranolol, alprenolol, bufetolol, oxprenolol, procainamide hydrochloride, disopyramide, ajmaline, quinidine sulfate, aprindine hydrochloride, propafenone hydrochloride, and mexiletine hydrochloride. (16) Vasodilators: for example, a calcium antagonist selected from diltiazem, nifedipine, diltiazem hydrochloride, verapamil, and nicardipine hydrochloride, oxyfedrine, tolazoline, hexobendine, bamethan, isosorbide dinitrate, trapidil, dipyridamole, dilazep hydrochloride, ifenprodil tartrate, cinepazide maleate, cyclandelate, cinnarizine, and pentoxifylline. (17) Antihypertensive diuretics: for example, hexamethonium bromide, pentolinium, mecamylamine, ecarazine, clonidine, diltiazem, nifedipine, furosemide, trichlormethiazide, methyclothiazide, hydrochlorothiazide, hydroflumethiazide, ethiazide, cyclopenthiazide, florothiazide, and ethacrynic acid. (18) Antidiabetic agents: for example, glymidine, glipizide, phenformin, buformin, metformin, glibenclamide, and tolbutamide. (19) Antitubercular agents: for example, isoniazid, ethambutol, and para-aminosalicylic acid. (20) Narcotic antagonists: for example, levallorphan, nalorphine, naloxone, and salts thereof (21) Hormonal agents: steroid hormones, for example, dexamethasone, hexestrol, methimazole, betamethasone, triamcinolone, triamcinolone acetonide, fluocinolone acetonide, prednisolone, hydrocortisone, and estriol. (22) Osteochondropathy preventing and treating agents: for example, non-peptidic osteogenesis-promotion enhancers such as prostaglandin A1 derivatives, vitamin D derivatives, vitamin $K_2$ derivatives, eicosapentaenoic acid derivatives, benzylphosphonate, bisphosphonic acid derivatives, sex-hormone derivatives, phenolsulfophthalein derivatives, benzothiopyran or benzothiepine derivatives, thienoindazole derivatives, menatetrenone derivatives, and helioxanthin derivatives, and peptidic osteogenesis-promotion enhancers. (23) Arthropathy treating agents: for example, antiinflammatory steroids such as p38MAP kinase inhibitors (e.g., thiazole-based compounds described in WO 00/64894 and the like), matrix-metalloprotease inhibitors (MMPI), prednisolone, hydrocortisone, methylprednisolone, dexa/betamethasone, and betamethasone, and non-steroidal antiinflammatory agents such as indomethacin, diclofenac, loxoprofen, ibuprofen, piroxicam, and sulindac. (24) Hydrochlorides for treating pollakiuria: for example, flavoxate, oxybutynin hydrochloride, and terodiline hydrochloride. (25) Antiandrogenic agents: for example, oxendolone, allylestrenol, chlormadinone acetate, gestonorone caproate, osaterone acetate, flutamide, and bicalutamide.

(26) Fat-soluble vitamins: vitamins K such as vitamins $K_1$, $K_2$, $K_3$ and $K_4$, folic acid (vitamin M), and the like. (27) Various derivatives of vitamins: for example, vitamin $D_3$ derivatives such as 5,6-trance-cholecalciferol, 2,5-hydroxycholecalciferol, and 1-α-hydroxycholecalciferol, and vitamin $D_2$ derivatives such as 5,6-trance-ergocalciferol. (28) Others such as hydroxycam, diacerein, megestrol acetate, nicergoline, and prostaglandins, as well as ischemic disease treating agents, immunologic disease treating agents, Alzheimer's disease treating agents, osteoporosis treating agents, angiogenesis treating agents, retinopathy treating agents, retinal vein occlusion treating agents, senile disciform macular degeneration treating agents, cerebral vasospasm treating agents, thrombosis treating agents, cerebral infarction treating agents, cerebral occlusion treating agents, intracerebral hemorrhage treating agents, subarachnoid hemorrhage treating agents, hypertensive encephalopathy treating agents, transient ischemic attack treating agents, multiinfarct dementia treating agents, arteriosclerosis treating agents, Huntington disease treating agents, brain tissue damage treating agents, optic neuropathy treating agents, glaucoma treating agents, ocular hypertension treating agents, retinal detachment treating agents, arthritis treating agents, antirheumatic agents, antisepsis agents, anti-septic shock agents, antiasthmatic agents, atopic dermatitis treating agents, allergic rhinitis treating agents, and the like are also usable.

In one embodiment of the present invention, a central nervous system enzyme inhibitory substance is used as a poorly water-soluble or water-insoluble active pharmaceutical ingredient. Examples of the central nervous system enzyme inhibitory substance include (2) tranquilizers and (3) antipsychotic agents mentioned above.

The poorly water-soluble or water-insoluble active pharmaceutical ingredient is a substance preferably having a water solubility of 10 mg/mL or less, more preferably 0.1 mg/mL or less, still more preferably 10 μg/mL or less, particularly preferably 1 μg/mL or less, and above all 0.9 μg/mL or less, at about 37° C. While the melting point of the active pharmaceutical ingredient is not particularly limited, it is preferably not lower than about 80° C. and not higher than about 350° C. While the structure of the active pharmaceutical ingredient is not particularly limited, the active pharmaceutical ingredient preferably contains one or more aromatic rings in the structural formula. For example, when the active pharmaceutical ingredient is 1-[2-fluoro-4-(1H-pyrazole-1-yl)phenyl]-5-methoxy-3-(1-phenyl-1H-pyrazole-5-yl)pyridazin-4(1H)-one, it preferably has a water solubility of 0.9 μg/mL at about 37° C.

[Enteric Base Material]

The enteric base material denotes a polymer whose dissolution under acidic conditions in the stomach is controlled, and which rapidly dissolves in an intestinal (gastrointestinal tract) environment. The enteric base material is an ingredient that is used in combination with methyl cellulose or an organic acid in the solid dispersion of the present invention, and is assumed to thereby act to maintain a supersaturation state of the active pharmaceutical ingredient. Generally, the pH changes in the gastrointestinal tract to reach 1 to 3.5 in the stomach, 5 to 6 in the duodenum, 6 to 7 in the jejunum, or 8 in the ileum. Therefore, a preferable enteric base material dissolves in a pH range of approximately 5.0 to 7.0, and preferably about 5.5 to about 6.5. Specific examples of such enteric base materials include hypromellose phthalate having degrees of substitution per monomer unit of 21 to 35% of carboxybenzoyl groups, 18 to 24% of methoxy groups, and 5 to 10% of hydroxypropoxy groups (for example, HP-50 and HP-55 from Shin-Etsu Chemical Co., Ltd.); hydroxypropylmethylcellulose acetate succinate having degrees of substitution per monomer unit of 20 to 26% of methoxyl groups, 5 to 10% of hydroxypropoxyl groups, 5 to 14% of acetyl groups, and 4 to 18% of succinoyl groups (for example, AQOAT-AS-LF, AS-MF, and AS-HG from Shin-Etsu Chemical Co., Ltd.); a copolymer of methacrylic acid and methyl methacrylate having a content of methacrylic acid units of 27.6% to 50.6% in dried raw materials (for example, Eudragit L100 and S100 from Evonik); a copolymer of methacrylic acid and ethyl acrylate having a content of methacrylic acid units of 46.0% to 50.6% in dried raw materials (for example, Eudragit L100-55 and L30D-55 from Evonik); and a copolymer of methacrylic acid, methyl acrylate, and methyl methacrylate having a content of methacrylic acid units of 9.2% to 12.3% in dried raw materials (for example, Eudragit FS30D from Evonik). One of these polymers as enteric base materials may be used alone, or two or more of them may be mixed for use.

The following respective conditions that may affect the pH range where each of the following enteric base materials dissolves are properties that may impart enteric properties in the present invention, although in conventional art, they may be defined as properties of the water-soluble polymer.

HPMCP (Hypromellose Phthalate):

Hypromellose phthalate having degrees of substitution per monomer unit of 21 to 35% of carboxybenzoyl groups, 18 to 24% of methoxy groups, and 5 to 10% of hydroxypropoxy groups.

HPMCAS (Hydroxypropylmethylcellulose Acetate Succinate):

Hydroxypropylmethylcellulose acetate succinate having degrees of substitution per monomer unit of 20 to 26% of methoxyl groups, 5 to 10% of hydroxypropoxyl groups, 5 to 14% of acetyl groups, and 4 to 18% of succinoyl groups.

Copolymers of Acrylic Acid and Methacrylic Acid:

A copolymer of methacrylic acid and methyl methacrylate having a content of methacrylic acid units of 27.6% to 50.6% in dried raw materials; a copolymer of methacrylic acid and ethyl acrylate having a content of methacrylic acid units of 46.0% to 50.6% in dried raw materials; and a copolymer of methacrylic acid, methyl acrylate, and methyl methacrylate having a content of methacrylic acid units of 9.2% to 12.3% in dried raw materials.

Among the enteric base materials used in the present invention, one or more selected from hydroxypropylmethylcellulose phthalate, hydroxypropylmethylcellulose acetate succinate, and methacrylic acid copolymers, for example, are also preferable.

The following are also preferable as enteric base materials used in the present invention:

1) hydroxypropylmethylcellulose phthalate or hydroxypropylmethylcellulose acetate succinate having degrees of substitution per monomer unit of not less than 18% and not more than 26% of methoxy groups, and not less than 5% and not more than 10% of hydroxypropoxy groups; and 2) a copolymer of acrylic acid and methacrylic acid having a content of methacrylic acid units of not less than 9% and not more than 51% in dried raw materials.

Note that the enteric base material used in the present invention may have properties as a base substrate to rapidly dissolve in an intestinal environment, and the final composition (solid dispersion) need not be enteric. That is, the solid dispersion of the present invention may dissolve in the stomach.

[Methyl Cellulose as the Water-Soluble Polymer]

The water-soluble polymer denotes a water-soluble polymer whose water solubility is pH-independent. That is, the enteric base material and the water-soluble polymer are herein distinguished in terms of whether the solubility is pH-dependent or not. The solid dispersion of the present invention contains methyl cellulose alone as the water-soluble polymer. Methyl cellulose is an ingredient that continues to be present in a solid state in the solid dispersion of the present invention, and is assumed to thereby act to maintain a supersaturation state of the active pharmaceutical ingredient. While the average molecular weight of methyl cellulose in the present invention is not particularly limited, it is preferably not less than 10000 and not more than 200000, and more preferably about 24,000 to 150,000. Furthermore, such methyl cellulose preferably has a viscosity at 20° C. of a 2% aqueous solution (Japanese Pharmacopoeia) of 3 to 1500 mPa·S, and more preferably 4 to 400 mPa·S. Methyl cellulose having a molecular weight in the above-mentioned range of molecular weights and methyl cellulose having a viscosity in the above-mentioned range of viscosities do not form high-viscosity gels in the aqueous solutions, and thus, can eliminate the risk of an excessive delay in the dissolution of the active pharmaceutical ingredient.

The organic acid is not particularly limited so long as it is an organic acid generally used in the field of pharmaceutical preparations. Examples of organic acids include adipic acid, ascorbic acid, benzoic acid, oleic acid, succinic acid, acetic acid, tartaric acid, sorbic acid, fumaric acid, lactic acid, maleic acid, malonic acid, citric acid, and malic acid. Fumaric acid, succinic acid, citric acid, tartaric acid, and malic acid are preferable, and fumaric acid and succinic acid are particularly preferable. One of these organic acids may be used alone, or two or more of them may be mixed for use.

[Solid Dispersion]

As used herein, the solid dispersion refers to a solid composition in which the above-described active pharmaceutical ingredient and other substances are homogeneously mixed. Moreover, in the present invention, the active pharmaceutical ingredient is present partially, preferably mostly, and more preferably completely in an amorphous state, in the solid dispersion. The amorphous state denotes a state of a substance having short-range order, rather than long-range order as in a crystal, and is identified as showing halo peaks in X-ray diffraction, for example. In the present invention, preferably 50% or more, more preferably 80% or more, still more preferably 90% or more, and even more preferably 95% or more, of the active pharmaceutical ingredient is present in an amorphous state.

The above-described other substances refer to substances other than the above-described active pharmaceutical ingredient, which are the enteric base material, methyl cellulose as the water-soluble polymer, the organic acid, and other additives. That is, the solid dispersion of the present invention is any of the following: a solid dispersion containing the amorphous active pharmaceutical ingredient, methyl cellulose as the water-soluble polymer, and the enteric base material; a solid dispersion containing the amorphous active pharmaceutical ingredient, methyl cellulose as the water-soluble polymer, the enteric base material, and the organic acid; and a solid dispersion containing the amorphous active pharmaceutical ingredient, the enteric base material, and the organic acid. While the solid dispersion of the present invention contains the enteric base material, the solubility of the solid dispersion itself, release properties of the drug from the solid dispersion, or dissolution properties of the solid dispersion need not necessarily be pH-dependent. While the proportions of the active pharmaceutical ingredient, the enteric base material, and the water-soluble polymer are not particularly limited, preferably, the proportion of the enteric base material to the active pharmaceutical ingredient is 200 to 600%, and the proportion of methyl cellulose to the active pharmaceutical ingredient is 50% to 150%; and more preferably, the proportion of the enteric base material to the active pharmaceutical ingredient is 350 to 450%, and the proportion of the water-soluble polymer to the active pharmaceutical ingredient is 75 to 125%. While the proportions of the active pharmaceutical ingredient, the enteric base material, and the organic acid are not particularly limited, preferably, the proportion of the enteric base material to the active pharmaceutical ingredient is 200 to 600%, and the proportion of the organic acid to the active pharmaceutical ingredient is 1% to 400%; and more preferably, the proportion of the enteric base material to the active pharmaceutical ingredient is 350 to 450%, and the proportion of the organic acid to the active pharmaceutical ingredient is 10 to 200%.

While the proportions of the active pharmaceutical ingredient, the enteric base material, the water-soluble polymer, and the organic acid are not particularly limited, preferably, the proportion of the enteric base material to the active pharmaceutical ingredient is 200 to 600%, the proportion of methyl cellulose to the active pharmaceutical ingredient is 50% to 150%, and the proportion of the organic acid to the active pharmaceutical ingredient is 1% to 400%; and more preferably, the proportion of the enteric base material to the active pharmaceutical ingredient is 350 to 450%, the proportion of the water-soluble polymer to the active pharmaceutical ingredient is 75 to 125%, and the proportion of the organic acid to the active pharmaceutical ingredient is 10 to 200%. It is desirable that the amount of residual organic solvent due to the additives in the solid dispersion be 0.1% or less, preferably 0.05% or less, and more preferably 0.01%, in terms of weight ratio in the solid dispersion. The residual organic solvent includes all substances generally used as organic solvents, and examples thereof include organic solvents such as alcohols, aromatic hydrocarbons, ethers, ketones, halogenated hydrocarbons, amides, sulfoxides, and mixtures of two or more of them. The amount of residual organic solvent can be quantified using gas chromatography, for example. It is desirable that the water content in the solid dispersion be 5.0% or less, preferably 3.0% or less, and more preferably 1.0%, in terms of weight ratio in the solid dispersion. The water content in the solid dispersion can be quantified using the Karl-Fischer titration method (16th Revised Japanese Pharmacopoeia), for example. Note that "%" used herein is intended to denote wt %, unless otherwise specified.

When the solid dispersion of the present invention contains methyl cellulose, the amorphous active pharmaceutical ingredient and methyl cellulose in a solid state are dispersed in the enteric base material in the solid dispersion. While not wishing to be bound by theory, it is assumed that in this solid dispersion, the enteric base material and methyl cellulose facilitate maintaining a supersaturation state of the active pharmaceutical ingredient in an amorphous state in the solution, which enhances the absorption properties of the active pharmaceutical ingredient. It is assumed that methyl cellulose, which is a water-soluble polymer having a high melting point or glass transition point and unlikely to melt or undergo a transition, is present with a particle size close to that during preparation in the solid dispersion, to prevent interaction between molecules of the active pharmaceutical ingredient, maintain the amorphous state in the solid dispersion, and also prevent interaction between molecules of the active pharmaceutical ingredient in the solution, thus contributing to an increase in dissolved concentration and the maintenance of supersaturation. Among the solid dispersions of the present invention, a solid dispersion in which the amorphous state is maintained is preferable.

Note that in the solid dispersion, the active pharmaceutical ingredient is in an amorphous state, and is also dispersed at a molecular level and is in a state energetically higher than a crystal; therefore, the active pharmaceutical ingredient is supersaturated, i.e., dissolved in the solution more than the case with a solubility in a stable crystalline form.

When the solid dispersion of the present invention contains methyl cellulose, the weight ratio of (1) the amorphous active pharmaceutical ingredient to (2) methyl cellulose as the sole water-soluble polymer and (3) the enteric base material in the solid dispersion is not limited, but the weight ratio of these ingredients is 1:1:3.5-4.5, for example, preferably 1:1:3.8-4.3, and more preferably 1:1:4.

When the solid dispersion of the present invention contains methyl cellulose, the weight ratio of (2) methyl cellulose as the water-soluble polymer in the solid dispersion is not particularly limited, but the weight ratio is about 1% to about 3000%, for example, preferably about 10% to about 1000%, and more preferably about 20% to about 200%, with respect to the active pharmaceutical ingredient.

The other additives are additives generally used in the field of pharmaceutical preparations, i.e., pharmacologically acceptable carriers such as various organic and inorganic carrier substances commonly used as pharmaceutical raw materials, and are added as excipients, lubricants, binders, disintegrators, and the like. Pharmaceutical additives such as preservatives, antioxidants, colorants, and sweetening agents can also be used, as required. Note, however, that the solid dispersion of the present invention need not contain an additive generally used as a plasticizer, although it may contain such an additive in an amount that does not impair the purpose of the present invention. When the solid dispersion of the present invention contains additives, these additives are preferably other than plasticizers.

That is, where a plasticizer reduces the dissolution properties, the solid dispersion of the present invention preferably does not contain the plasticizer, or may contain the plasticizer in an amount that does not impair the dissolution properties. Where a plasticizer does not affect the dissolution properties, the solid dispersion of the present invention does not contain or may contain the plasticizer, and preferably, the solid dispersion does not contain the plasticizer, or may contain the plasticizer in an amount that does not impair the dissolution properties. Where a plasticizer enhances the dissolution properties, the solid dispersion of the present invention may or may not contain the plasticizer. In any case, where a plasticizer does not significantly enhance the dissolution properties, the solid dispersion of the present invention preferably does not contain the plasticizer, or may contain the plasticizer in an amount that does not impair the dissolution properties.

Examples of plasticizers, which are additives generally used as plasticizers, include polyethylene glycol 400 (Macrogol 400), polyethylene glycol 600 (Macrogol 600), polyethylene glycol 1500 (Macrogol 1500), polyethylene glycol 4000 (Macrogol 4000), polyethylene glycol 6000 (Macrogol 6000), propylene glycol, glycerol monostearate, isopropyl myristate, triacetin, glycerol, glycerol fatty acid ester, triethyl citrate, polysorbate 80, diethyl phthalate, and dibutyl phthalate.

Suitable examples of usable excipients include lactose, white soft sugar, D-mannitol, starch, crystalline cellulose, sucrose, porous starch, mannitol, calcium silicate, magnesium aluminometasilicate, light anhydrous silicic acid, white soft sugar/starch spherical granules, crystalline cellulose/carboxymethyl cellulose, and hydroxypropyl starch. Suitable examples of lubricants include crystalline cellulose, magnesium stearate, calcium stearate, talc, colloidal silica, corn starch, and magnesium oxide. Suitable examples of binders include crystalline cellulose, white soft sugar, D-mannitol, and dextrin. Suitable examples of disintegrators include starch, carboxymethyl cellulose, carboxymethyl cellulose calcium, croscarmellose sodium, carmellose calcium, low substituted hydroxypropyl cellulose, sodium starch glycolate, and partially pregelatinized starch. Suitable examples of antioxidants include sulfite and ascorbic acid. One of these additives may be used alone, or two or more of them may be mixed for use.

[Method of Producing the Solid Dispersion]

While the method of producing the solid dispersion of the present invention is not particularly limited, the solid dispersion may be prepared by a hot-melt extrusion method (HME method), a solvent method, a melt-solvent method, or the like. Preferable among the above is the hot-melt extrusion method, by which the solid dispersion is obtained by forming a homogeneous kneaded product of constituents in the form of a melt, extruding the kneaded product, and molding the extrudate. The solid dispersion can also be used after being cut into a given size in accordance with the purpose.

In the hot-melt extrusion method, an extruder having screw(s) in a cylinder (e.g., a single screw extruder and a twin screw extruder) or an injection apparatus of an injection molding machine (e.g., a twin screw-type extruder) can be used. Among the above, an injection apparatus of a twin screw-type extruder is preferable. In this case, the active pharmaceutical ingredient and other substances are injected through the hopper into the apparatus maintained at an appropriate hot-melt temperature, and the screws are rotated. This causes the active pharmaceutical ingredient to be hot-melted, and simultaneously mixed with the other substances and extruded. After cooling, a solid dispersion with a homogeneous composition is obtained.

The method of producing the solid dispersion using the hot-melt extrusion method includes the steps of, for example, physically mixing the active pharmaceutical ingredient in an amorphous state with methyl cellulose and/or the organic acid and the enteric base material, heating and melting the mixture under elevated pressure, and then rapidly cooling the melt. Upon heating under elevated pressure as described above, the enteric base material having a low melting point melts first, and then the active pharmaceutical ingredient melts to dissolve into the melted enteric base material described above. Further continued heating causes the above-described active pharmaceutical ingredient to be dispersed at a molecular level in the enteric base material. At this time, a solid state is maintained because the melting point(s) of methyl cellulose and/or the organic acid are higher than the elevated temperature.

The solid dispersion of the present invention can be ground using an appropriate grinder to be readily formed into solid dispersion particles having a given particle size, which can be directly utilized as powders or granules. Moreover, the ground fine particles can be admixed as appropriate with other additives, and then subjected to necessary steps for making pharmaceutical preparations, to be utilized as tablets, granules, fine granules, capsules, injections, and the like. As the other additives here, pharmacologically acceptable carriers such as various organic and inorganic carrier substances commonly used as pharmaceutical raw materials are used, and are added as excipients, lubricants, binders, disintegrators, surfactants, and the like. Pharmaceutical additives such as preservatives, antioxidants, colorants, and sweetening agents can also be used, as required. Suitable examples of usable excipients include lactose, white soft sugar, D-mannitol, starch, crystalline cellulose, sucrose, porous starch, mannitol, calcium silicate, magnesium aluminometasilicate, light anhydrous silicic acid, white soft sugar/starch spherical granules, crystalline cellulose/carboxymethyl cellulose, and hydroxypropyl starch. Suitable examples of lubricants include crystalline cellulose, magnesium stearate, calcium stearate, talc, colloidal silica, corn starch, and magnesium oxide. Suitable examples of binders include crystalline cellulose, white soft sugar, D-mannitol, dextrin, hydroxypropylcellulose, hydroxypropylmethylcellulose, and polyvinyl pyrrolidone. Suitable examples of disintegrators include starch, carboxymethyl cellulose, carboxymethyl cellulose calcium, croscarmellose sodium, sodium carboxymethyl starch, methyl cellulose, croscarmellose sodium, carmellose calcium, low substituted hydroxypropyl cellulose, sodium starch glycolate, and partially pregelatinized starch. Suitable examples of antioxidants include sulfite and ascorbic acid. One of these additives may be used alone, or two or more of them may be mixed for use. One of these additives may be used alone, or two or more of them may be mixed for use.

A pharmaceutical preparation composed of or containing the solid dispersion obtained by the production method of the present invention can be safely administered to a mammal (e.g., a rat, a mouse, a guinea pig, a monkey, a cow, a dog, a pig, or a human) orally or parenterally (e.g., intravenously, intramuscularly, subcutaneously, into an organ, intranasally, intracutaneously, intraocularly, intracerebrally, intrarectally, intravaginally, intraabdominally, or directly administered into a lesion), depending on the type and the like of the active pharmaceutical ingredient. While the dose of the active pharmaceutical ingredient contained in the pharmaceutical preparation composed of or containing the solid dispersion obtained by the production method of the present invention varies depending on the type and the like of the active pharmaceutical ingredient, the subject for administration, the route of administration, the target disease, symptoms, and the like, when the active pharmaceutical ingredient is 1-[2-fluoro-4-(1H-pyrazole-1-yl)phenyl]-5-methoxy-3-(1-phenyl-1H-pyrazole-5-yl)pyridazin-4(1H)-one, which is a central nervous system enzyme inhibitory substance, for example, in the case of oral administration to a schizophrenic patient (adult weighing about 60 kg), it is administered typically in an amount of about 0.1 to about 20 mg/kg body weight, preferably about 0.2 to about 10 mg/kg body weight, and more preferably about 0.5 to about 10 mg/kg body weight, per dose, and this amount of the active pharmaceutical ingredient is desirably administered in a single or several doses (e.g., three times) a day.

The present invention also provides a method of maintaining, in a solid dispersion produced by a hot-melt extrusion method, the solid dispersion containing an amorphous active pharmaceutical ingredient, one or more selected from methyl cellulose and organic acids, and an enteric base material, wherein when the solid dispersion contains methyl cellulose, the solid dispersion does not contain a water-soluble polymer other than methyl cellulose, a supersaturation state in the solid dispersion by using the above-described methyl cellulose in a solid state.

EXAMPLES

The present invention will be hereinafter described in more detail with referential examples and examples; however, the present invention is not limited to these examples in any sense. Note that in the following examples and comparative examples, products conforming to 16th Revised Japanese Pharmacopoeia or Japan Pharmaceutical Excipients 2013 were used as pharmaceutical additives.

Referential Example 1

Uncoated tablets containing 1-[2-fluoro-4-(1H-pyrazole-1-yl)phenyl]-5-methoxy-3-(1-phenyl-1H-pyrazole-5-yl)pyridazin-4(1H)-one (hereinafter denoted as compound A) were prepared to have the composition ratio shown below.

In a fluidized bed granulator dryer (FD-5S from Powrex Corporation), 52.82 g of compound A (content-adjusted), 3694 g of D-mannitol (weight-adjusted), 897.1 g of crystalline cellulose, and 263.9 g of sodium starch glycolate were placed and mixed while preheating, and 2638 g of an aqueous solution containing 158.3 g of hydroxypropylcellulose dissolved in 2480 g of purified water was sprayed thereto, thus obtaining a granulated powder. A milled powder was obtained by passing 4651 g of the obtained granulated powder through Power Mill (P-3 from Showa Kagaku Kikai Co., Ltd.). In a tumbler mixer (15 L from Showa Kagaku Kikai Co., Ltd.), 4435 g of the milled powder was placed together with 138.6 g of crystalline cellulose and 46.20 g of magnesium stearate and mixed, thus obtaining a mixed powder. The mixed powder was tableted using a rotary tableting machine (Collect 12HUK from Kikusui Seisakusho Ltd.) to give 100 mg per tablet with punches 6 mm in diameter, thus obtaining uncoated tablets.

<Composition of the Uncoated Tablets Containing Compound A>

| | |
|---|---|
| Compound A | 1 mg |
| D-mannitol | 70 mg |
| Crystalline cellulose | 20 mg |
| Hydroxypropylcellulose | 3 mg |
| Sodium starch glycolate | 5 mg |
| Magnesium stearate | 1 mg |
| Total | 100 mg |

In a film coating machine (DRC-500 from Powrex Corporation), 2991 g of the obtained uncoated tablets were placed, and 1106.4 g of a coating solution having the composition ratio shown below was sprayed thereto, thus obtaining rapidly disintegrating tablets weighing about 103.05 mg per tablet.

<Composition of the Coating Solution>

| | |
|---|---|
| Hypromellose | 2.25 mg |
| Macrogol 6000 | 0.5 mg |
| Titanium oxide | 0.25 mg |
| Iron sesquioxide | 0.017 mg |
| Yellow iron sesquioxide | 0.033 mg |
| Purified water | 27.45 mg |
| Total (solids content) | 30.5 (3.05) mg |

Referential Example 2

Uncoated tablets containing compound A having the composition ratio shown below were produced as follows. In a fluidized bed granulator dryer (FD-5S from Powrex Corporation), 264.2 g of compound A (content-adjusted), 3483 g of D-mannitol (weight-adjusted), 897.1 g of crystalline cellulose, and 263.9 g of sodium starch glycolate were placed and mixed while preheating, and 2638 g of an aqueous solution containing 158.3 g of hydroxypropylcellulose dissolved in 2480 g of purified water was sprayed thereto, thus obtaining a granulated powder. A milled powder was obtained by passing 4651 g of the obtained granulated powder through Power Mill (P-3 from Showa Kagaku Kikai Co., Ltd.). In a tumbler mixer (15 L from Showa Kagaku Kikai Co., Ltd.), 4435 g of the milled powder was placed together with 138.6 g of crystalline cellulose and 46.20 g of magnesium stearate and mixed, thus obtaining a mixed powder. The mixed powder was tableted using a rotary tableting machine (Collect 12HUK from Kikusui Seisakusho Ltd.) to give 100 mg per tablet with punches 6 mm in diameter, thus obtaining uncoated tablets.

<Composition of the Uncoated Tablets Containing Compound A>

| Compound A | 5 mg |
|---|---|
| D-mannitol | 66 mg |
| Crystalline cellulose | 20 mg |
| Hydroxypropylcellulose | 3 mg |
| Sodium starch glycolate | 5 mg |
| Magnesium stearate | 1 mg |
| Total | 100 mg |

In a film coating machine (DRC-500 from Powrex Corporation), 2991 g of the obtained uncoated tablets were placed, and 1035.1 g of the coating solution having the composition ratio shown in Reference Example 1 was sprayed thereto, thus obtaining rapidly disintegrating tablets weighing about 103.05 mg per tablet.

Referential Example 3

Uncoated tablets containing compound A having the composition ratio shown below were produced as follows. In a fluidized bed granulator dryer (FD-5S from Powrex Corporation), 528.2 g of compound A (content-adjusted), 3219 g of D-mannitol (weight-adjusted), 897.1 g of crystalline cellulose, and 263.9 g of sodium starch glycolate were placed and mixed while preheating, and 2638 g of an aqueous solution containing 158.3 g of hydroxypropylcellulose dissolved in 2480 g of purified water was sprayed thereto, thus obtaining a granulated powder. A milled powder was obtained by passing 4651 g of the obtained granulated powder through Power Mill (P-3 from Showa Kagaku Kikai Co., Ltd.). In a tumbler mixer (15 L from Showa Kagaku Kikai Co., Ltd.), 4435 g of the milled powder was placed together with 138.6 g of crystalline cellulose and 46.20 g of magnesium stearate and mixed, thus obtaining a mixed powder. The mixed powder was tableted using a rotary tableting machine (Collect 12HUK from Kikusui Seisakusho Ltd.) to give 100 mg per tablet with punches 6 mm in diameter, thus obtaining uncoated tablets.

<Composition of the Uncoated Tablets Containing Compound A>

| Compound A | 10 mg |
|---|---|
| D-mannitol | 61 mg |
| Crystalline cellulose | 20 mg |
| Hydroxypropylcellulose | 3 mg |
| Sodium starch glycolate | 5 mg |
| Magnesium stearate | 1 mg |
| Total | 100 mg |

In a film coating machine (DRC-500 from Powrex Corporation), 2991 g of the obtained uncoated tablets were placed, and 1049.0 g of a coating solution having the composition ratio shown in Referential Example 1 was sprayed thereto, thus obtaining rapidly disintegrating tablets weighing about 103.05 mg per tablet.

Referential Example 4

Uncoated tablets containing compound A having the composition ratio shown below were produced as follows. In a fluidized bed granulator dryer (FD-5S from Powrex Corporation), 1320 g of compound A (content-adjusted), 2426 g of D-mannitol (weight-adjusted), 897.1 g of crystalline cellulose, and 263.9 g of sodium starch glycolate were placed and mixed while preheating, and 2638 g of an aqueous solution containing 158.3 g of hydroxypropylcellulose dissolved in 2480 g of purified water was sprayed thereto, thus obtaining a granulated powder. A milled powder was obtained by passing 4651 g of the obtained granulated powder through Power Mill (P-3 from Showa Kagaku Kikai Co., Ltd.). In a tumbler mixer (15 L from Showa Kagaku Kikai Co., Ltd.), 4435 g of the milled powder was placed together with 138.6 g of crystalline cellulose and 46.20 g of magnesium stearate and mixed, thus obtaining a mixed powder. The mixed powder was tableted using a rotary tableting machine (Collect 12HUK from Kikusui Seisakusho Ltd.) to give 100 mg per tablet with punches 6 mm in diameter, thus obtaining uncoated tablets.

<Composition of the Uncoated Tablets Containing Compound A>

| Compound A | 25 mg |
|---|---|
| D-mannitol | 46 mg |
| Crystalline cellulose | 20 mg |
| Hydroxypropylcellulose | 3 mg |
| Sodium starch glycolate | 5 mg |
| Magnesium stearate | 1 mg |
| Total | 100 mg |

In a film coating machine (DRC-500 from Powrex Corporation), 2991 g of the obtained uncoated tablets were placed, and 1030.0 g of the coating solution having the composition ratio shown in Referential Example 1 was sprayed thereto, thus obtaining rapidly disintegrating tablets weighing about 103.05 mg per tablet.

[Method of Producing Solid Dispersions (Examples 1 to 11 and Comparative Examples 1 to 3)]

Raw materials were weighed in the amounts of the formulation shown in Table 1 for each of the examples and comparative examples. The weighed raw materials were manually mixed in a mortar for 1 to 3 minutes. An appropriate amount of the mixed powder was melt-extruded using a twin screw extruder (conical screw HB-1 from Imoto Machinery Co., Ltd.) equipped with a die having a 6-mm-diameter aperture, set at a barrel temperature of 170 to 180° C., and set at a screw rotation speed of 80 rpm, thus obtaining a molded product of the solid dispersion. The obtained molded product was coarsely crushed in a coffee mill (SM-1 from Iuchi Seieido Co., Ltd.), as required, and then ground in a ball mill (SPEX8000 from SPEX Sample Prep). The ground product was subsequently screened through a screen with a mesh size of 106 μm, and then the screened product was collected, thus obtaining a ground powder of the solid dispersion.

Note that the compound denoted as "Compound A" in Table 1 is 1-[2-fluoro-4-(1H-pyrazole-1-yl)phenyl]-5-methoxy-3-(1-phenyl-1H-pyrazole-5-yl)pyridazin-4(1H)-one, which is a poorly water-soluble compound having at least one aromatic ring.

TABLE 1-1

Formulation

Amounts (g) of Formulation

| Raw Material Name | Comparative Example 1 | Example 1 | Example 2 | Example 3 | Example 4 | Example 5 | Comparative Example 2 | Example 6 |
|---|---|---|---|---|---|---|---|---|
| Compound A* | 10 | 10 | 4.5 | 10 | 56 | 10 | 4.5 | 4.5 |
| HPMCP | 40 | 40 | 18 | 40 | 224 | 40 | 18 | 18 |
| Methyl Cellulose | — | 10 | 4.5 | 10 | 56 | 10 | — | 4.5 |
| Fumaric Acid | — | — | — | 10 | 56 | — | — | 1.35 |
| Succinic Acid | — | — | — | — | — | 10 | — | — |
| Polyvinyl Alcohol | — | — | — | — | — | — | 4.5 | — |

*1-[2-Fluoro-4-(1H-Pyrazole-1-yl)Phenyl]-5-Methoxy-3-(1-Phenyl-1H-Pyrazole-5-yl)Pyridazin-4(1H)-one

TABLE 1-2

Formulation

Amounts (g) of Formulation

| Raw Material Name | Example 11 | Example 7 | Example 8 | Example 9 | Comparative Example 3 | Example 10 |
|---|---|---|---|---|---|---|
| Compound A | 7 | — | — | — | 4.5 | 5 |
| Nifedipine | — | 4 | 3.5 | 3 | — | — |
| HPMCP | 28 | 16 | 14 | 12 | — | 20 |
| Methyl Cellulose | 7 | 4 | 3.5 | 3 | 4.5 | — |
| Fumaric Acid | — | — | — | 3 | — | 5 |
| PVP | — | — | — | — | 18 | — |
| Light Anhydrous Silicic Acid | 2.1 | — | — | — | — | — |

*1-[2-Fluoro-4-(1H-Pyrazole-1-yl)Phenyl]-5-Methoxy-3-(1-Phenyl-1H-Pyrazole-5-yl)Pyridazin-4(1H)-one

[Testing Method]

The following dissolution tests (dissolution tests 1 and 2) were conducted on the solid dispersions produced as described above.

Dissolution Test 1
Testing Method:

As a test solution, 900 mL of USP phosphate buffer (pH 6.8) at 37° C. was used, and a test was conducted in a dissolution tester (NTR-6200AC from Toyama Sangyo Co., Ltd.) in accordance with the Japanese Pharmacopoeia dissolution test, second method (paddle method), at a paddle rotation speed of 100 rpm. At every given time, 10 mL of the dissolution test solution was sampled, and then the sampled solution was filtered. Acetonitrile was added to 5 mL of the filtered sampled solution to a volume of 10 mL, and then the concentration of the active pharmaceutical ingredient in the diluted solution was measured using UPLC (ACQUITY UPLC System from WATERS).

Dissolution Test 2
Testing Method:

As a test solution, 900 mL of USP phosphate buffer (pH 6.8) at 37° C. was used, and a test was conducted in a dissolution tester (NTR-6200AC from Toyama Sangyo Co., Ltd.) in accordance with the Japanese Pharmacopoeia dissolution test, second method (paddle method), at a paddle rotation speed of 100 rpm. At every given time, 10 mL of the dissolution test solution was sampled, and then the sampled solution was filtered. Ethanol was added to 5 mL of the filtered sampled solution to a volume of 10 mL, and then the concentration of the active pharmaceutical ingredient in the diluted solution was measured using an ultraviolet-visible spectrophotometer (UV-1800 from Shimadzu Corporation).

X-Ray Powder Diffraction Measurements:

X-ray powder diffraction measurements were conducted using an X-ray powder diffraction apparatus (RINT-TTR2 from RIGAKU) under the following conditions, for example:

a voltage of 50 kV, a scanning speed of 40.0°/min, and a current of 300 mA.

[Results]

Results of conducting the tests described in Test Examples 1 to 8 below were as follows.

Test Example 1

Dissolution test 1 was conducted on each of the ground powders of the solid dispersions according to Comparative Example 1 and Example 1 in an amount equivalent to about 50 mg of the active pharmaceutical ingredient. As shown in Table 2, the ground powder of the solid dispersion according to Example 1 to which methyl cellulose was added showed remarkably high concentrations of the active pharmaceutical ingredient at all of the measured times, compared to the ground powder of the solid dispersion according to Comparative Example 1 not containing methyl cellulose.

These results demonstrated the effect of using methyl cellulose alone as the water-soluble polymer added to the solid dispersion of the present invention.

Test Example 2

Dissolution test 1 was conducted on each of the ground powders of the solid dispersions according to Comparative Example 1, Example 2, Example 4, and Example 10 in an amount equivalent to about 20 mg of the active pharmaceutical ingredient. As shown in Table 2, the ground powder of the solid dispersion according to Example 2 to which methyl cellulose was added, or the ground powder of the solid dispersion according to Example 10 to which fumaric acid was added, showed remarkably high concentrations of the active pharmaceutical ingredient at all of the measured times, compared to the ground powder of the solid dispersion according to Comparative Example 1 containing neither methyl cellulose nor fumaric acid. The ground powder of the solid dispersion according to Example 4 containing methyl cellulose and fumaric acid showed a more remarkably high concentration, compared to the ground powders of the solid dispersions according to Examples 2 and 10.

These results demonstrated the effect of adding each of methyl cellulose and the organic acid to the solid dispersion of the present invention.

Test Example 3

Dissolution test 1 was conducted on each of the ground powders of the solid dispersions according to Examples 1, 3 and 5 in an amount equivalent to about 50 mg of the active pharmaceutical ingredient. As shown in Table 2, the solid dispersions according to Examples 3 and 5 to which the organic acids were added showed dissolution properties superior to those of the solid dispersion according to Example 1 showing remarkably improved dissolution properties through the addition of methyl cellulose. That is, the effect of adding the organic acids to the solid dispersions of the present invention was demonstrated.

Test Example 4

Dissolution test 1 was conducted on each of the ground powders of the solid dispersions according to Comparative Example 1, Example 2 and Comparative Example 2 in an amount equivalent to about 20 mg of the active pharmaceutical ingredient. As shown in Table 2, the solid dispersion according to Example 2 containing methyl cellulose showed dissolution properties remarkably superior to those of the solid dispersion according to Comparative Example 1 not containing methyl cellulose and the solid dispersion according to Comparative Example 2 containing PVA instead of methyl cellulose.

These results revealed that the solid dispersion of the present invention in which MC was used alone as the water-soluble polymer has effects superior to that of the solid dispersion in which the other water-soluble polymer was used.

Test Example 5

Dissolution test 1 was conducted on each of the ground powders of the solid dispersions according to Examples 11 and 6 containing an amount of about 20 mg of the active pharmaceutical ingredient. As shown in Table 2, the solid dispersions according to both the examples showed remarkably high dissolution properties by containing MC. In particular, compared to the solid dispersion according to Example 11 containing light anhydrous silicic acid that is acid in the purified water, the solid dispersion according to Example 6 containing an equal amount of fumaric acid showed more remarkably superior dissolution properties. These results demonstrated that the effect of adding the organic acid is superior to the effect of adding the inorganic acid in the solid dispersions of the present invention.

Test Example 6

Dissolution test 2 was conducted on each of the ground powders of the solid dispersions according to Examples 7, 8 and 9 in an amount equivalent to 20 mg of the active pharmaceutical ingredient. As shown in Table 2, the effect of increasing the amount of dissolution obtained with methyl cellulose or fumaric acid was also confirmed for the case containing nifedipine as the active pharmaceutical ingredient, as with the case containing compound A.

Test Example 7

Dissolution test 1 was conducted on each of the ground powders of the solid dispersions according to Example 2 and Comparative Example 3 in an amount equivalent to 20 mg of the active pharmaceutical ingredient. As shown in Table 2, the solid dispersion according to Comparative Example 3 containing the water-soluble base material instead of the enteric base material showed an amount of dissolution smaller than that of the solid dispersion according to Example 2. That is, the effect of the enteric base material as the base material in the solid dispersion of the present invention was revealed.

Test Example 8

Dissolution test 1 was conducted on each of the ground powders of the solid dispersions according to Comparative Example 1 and Example 10 in an amount equivalent to 20 mg of the active pharmaceutical ingredient. As shown in Table 2, the solid dispersion according to Example 10 to which the organic acid was added showed an amount of dissolution greater than that of the solid dispersion according to Comparative Example 1. That is, the effect of adding the organic acid to the solid dispersion of the present invention was demonstrated.

Test Example 9

X-ray powder diffraction measurements were conducted on the ground powders of the solid dispersions according to Comparative Examples 1 to 3 and Examples 1 to 11, and fumaric acid. As a result, as shown in FIGS. 1 to 15, each of the analytes showed halo peaks or peaks originating from fumaric acid only, which confirmed that the active pharmaceutical ingredient was amorphous.

TABLE 2

Results of Dissolution Tests

| | | Amount Equivalent to Active Pharmaceutical Ingredient (mg) | Dissolution Time (Min) | | | | | | | |
|---|---|---|---|---|---|---|---|---|---|---|
| | | | 5 | 10 | 15 | 30 | 60 | 120 | 180 | 240 |
| Dissolution Concentration ($\mu$g/mL) | Comparative Example 1 | 50 | 8.16 | 5.44 | 4.72 | 4.04 | 3.49 | 3.16 | 2.97 | 2.90 |
| | Example 1 | 20 | 4.82 | 4.75 | 4.61 | 4.33 | 4.00 | — | — | — |
| | Example 1 | 50 | 29.89 | 26.47 | 23.28 | 17.56 | 13.39 | 10.27 | 8.76 | 7.94 |
| | Example 2 | 20 | 6.43 | 6.56 | 6.57 | 6.41 | 6.27 | — | — | — |

TABLE 2-continued

Results of Dissolution Tests

| | Amount Equivalent to Active Pharmaceutical Ingredient (mg) | Dissolution Time (Min) | | | | | | | |
|---|---|---|---|---|---|---|---|---|---|
| | | 5 | 10 | 15 | 30 | 60 | 120 | 180 | 240 |
| Example 3 | 50 | 34.07 | 31.33 | 28.64 | 22.56 | 16.68 | 12.46 | 10.56 | 9.37 |
| Example 4 | 20 | 16.30 | 16.54 | 16.43 | 15.96 | 15.20 | — | — | — |
| Example 5 | 50 | 41.93 | 36.25 | 30.52 | 20.92 | 14.98 | 11.46 | 10.07 | 9.13 |
| Comparative Example 2 | 20 | 5.16 | 4.12 | 5.02 | 4.75 | 4.49 | — | — | — |
| Example 6 | 20 | 14.87 | 15.04 | 14.88 | 14.50 | 13.70 | — | — | — |
| Example 11 | 20 | 1.74 | 1.93 | 2.06 | 2.24 | 2.40 | — | — | — |
| Example 7 | 20 | 57.51 | 65.75 | 64.75 | 63.38 | 59.63 | — | — | — |
| Example 8 | 20 | 74.93 | 78.74 | 79.68 | 79.24 | 77.49 | — | — | — |
| Example 9 | 20 | 82.43 | 86.23 | 86.55 | 86.55 | 86.55 | — | — | — |
| Comparative Example 3 | 20 | 1.32 | 1.88 | 2.27 | 2.66 | 2.74 | — | — | — |
| Example 10 | 20 | 8.43 | 9.41 | 7.93 | 5.66 | 4.13 | — | — | — |

INDUSTRIAL APPLICABILITY

According to the present invention, there is provided a solid dispersion having improved solubility and absorption properties of an active pharmaceutical ingredient. The present invention therefore greatly contributes to the development of pharmaceutical industry and its related industries.

The invention claimed is:

1. A solid dispersion comprising:
   (1) an amorphous active pharmaceutical ingredient;
   (2) at least one ingredient selected from the group consisting of methyl cellulose and an organic acid; and
   (3) an enteric base material, wherein
   when the solid dispersion comprises methyl cellulose, the solid dispersion does not comprise a water-soluble polymer other than methyl cellulose, and
   the active pharmaceutical ingredient is a poorly water-soluble or water-insoluble central nervous system enzyme inhibitory substance or vasodilator.

2. The solid dispersion according to claim 1, wherein a supersaturation state is maintained.

3. The solid dispersion according to claim 1, wherein the active pharmaceutical ingredient has a melting point not lower than about 80° C. and not higher than about 350° C.

4. The solid dispersion according to claim 1, wherein the active pharmaceutical ingredient has a water solubility of less than 10 mg/mL at about 37° C.

5. The solid dispersion according to claim 1, which is produced by a hot-melt extrusion method (HME method).

6. The solid dispersion according to claim 1, wherein the solid dispersion comprises methyl cellulose, wherein the weight ratio of the methyl cellulose to the active pharmaceutical ingredient is about 1% to 3000%.

7. The solid dispersion according to claim 1, comprising at least one organic acid.

8. The solid dispersion according to claim 1, wherein the enteric base material is at least one base material selected from the group consisting of hydroxypropylmethylcellulose phthalate, hydroxypropylmethylcellulose acetate succinate, and a methacrylic acid copolymer.

9. The solid dispersion according to claim 7, wherein the organic acid is selected from the group consisting of fumaric acid, citric acid, succinic acid, and tartaric acid.

10. A pharmaceutical composition comprising the solid dispersion according to claim 1 and a pharmaceutically acceptable additive.

11. A method of maintaining a supersaturation state of an active pharmaceutical ingredient in a solid dispersion produced by a hot-melt extrusion method (HME method),
   comprising combining an amorphous active pharmaceutical ingredient, at least one ingredient selected from the group consisting of methyl cellulose and an organic acid, and an enteric base material in a solid dispersion,
   wherein when the solid dispersion comprises methyl cellulose, the solid dispersion does not comprise a water-soluble polymer other than methyl cellulose,
   and producing the solid dispersion by an HME method.

12. A method of producing a solid dispersion comprising combining an amorphous active pharmaceutical ingredient, at least one ingredient selected from the group consisting of methyl cellulose and an organic acid, and an enteric base material,
   wherein when the solid dispersion comprises methyl cellulose, the solid dispersion does not comprise a water-soluble polymer other than methyl cellulose.

* * * * *